United States Patent [19]
Timmons

[11] Patent Number: 4,759,227
[45] Date of Patent: Jul. 26, 1988

[54] LYSIMETER

[76] Inventor: Robert D. Timmons, R.F.D. Meadowdale Rd., Prairie Du Sac, Wis. 53578

[21] Appl. No.: 853,871

[22] Filed: Apr. 21, 1986

Related U.S. Application Data

[62] Division of Ser. No. 526,387, Aug. 25, 1983, Pat. No. 4,692,287.

[51] Int. Cl.⁴ ............................................. G01N 1/14
[52] U.S. Cl. .................................. 73/863.23; 73/73; 73/864.34
[58] Field of Search ...................... 73/155, 38, 73, 76, 73/863.23, 864.34; 166/264

[56] References Cited

U.S. PATENT DOCUMENTS

| | | | |
|---|---|---|---|
| 3,054,761 | 9/1962 | Moore et al. | 264/49 X |
| 3,318,140 | 5/1967 | Shields et al. | 73/73 |
| 3,843,570 | 10/1974 | Murayama | 264/49 X |
| 3,945,247 | 3/1976 | Anderson | 73/155 |
| 4,068,525 | 1/1978 | Skaling | 73/73 |
| 4,548,266 | 10/1985 | Burklund | 166/264 X |

FOREIGN PATENT DOCUMENTS 2101234 8/1972 Fed. Rep. of Germany ... 76/864.34

Primary Examiner—Stewart J. Levy
Assistant Examiner—Kevin D. O'Shea
Attorney, Agent, or Firm—Dean P. Edmundson

[57] ABSTRACT

An improved lysimeter is described for collecting soil water which is truly representative of the soil water contained in the soil at selected locations. The lysimeter contains a chamber and a filter section which is a rigid, porous fluoroplastic and through which moisture from the soil surrounding the lysimeter may pass into the chamber. The invention also includes a process for using the lysimeter to recover soil moisture in the lysimeter chamber.

8 Claims, 2 Drawing Sheets

LYSIMETER

CROSS-REFERENCE TO RELATED APPLICATION

This application is a division of my copending application Ser. No. 526,387, filed Aug. 25, 1983 now U.S. Pat. No. 4,692,287.

FIELD OF THE INVENTION

This invention relates to lysimeters. More particularly, this invention relates to lysimeters, and processes for using, in which a unique filter section is incorporated.

BACKGROUND

It is important to know the nature and character of soil at selected locations in the vadose or unsaturated zone to determine if it may contain toxic materials or may be contaminated in some way which would make it suitable or unsuitable for specific purposes.

Water, which is contained within the soil, is representative of the soil in many respects, and the art has sought effective ways to collect the soil water at selected locations so that the water obtained may be analyzed, its contents identified, and their concentrations determined.

A method used in early attempts to recover soil water involved taking a sample of the soil and putting it under pressure to mechanically squeeze out the water. Devices were later developed called lysimeters which contain a sampling chamber and which use a vacuum to draw moisture from the soil through a filter into the sampling chamber. These devices have their limitations and they introduce inaccuracies in the collection of the water so that the soil moisture recovered has not been truly representative of the soil moisture under test. In an effort to reduce these inaccuracies there were attempts to use polyethylene porous tubes in the lysimeter. Then the focus of the art was turned to the use of porous ceramic filters, and attempts were made to preclean and treat these ceramic filters by leaching the porous ceramic material with hydrochloric acid followed by rinsing with deionized water. The porous ceramic filters were found to absorb or to interfere with the chemical constituents $NO_4$, $NO_3$, $NO_2$, $PO_4$, P and S especially when the sorptive capacity of the soil is less than that of the ceramic material. The porous ceramic filters were found to attenuate concentrations of Ni, Cu, Pb, $Z_n$, Fe and Mg, and were found to be unsuitable for fecal coliform analysis.

When using porous ceramic materials in the lysimeter, the porous ceramic material usually has been attached to a polyvinylchloride (PVC) tubing by use of an adhesive, but it has been found that both the PVC tubing and the adhesive used to secure it contribute to inaccuracies of the collected sample. Further, the ceramics are extremely fragile and it is difficult to assemble the ceramic filters in lysimeters, to install the lysimeters in a selected location and to remove the soil water collected without fracturing or breaking the ceramic materials.

An object of the present invention is to discover how to make an improved filter material which is structurally strong and chemically inert which can be used in a lysimeter through which moisture from the soil may be passed and then recovered from the lysimeter for testing, without disturbing the characteristics and contents of the soil moisture and without contributing elements to or subtracting elements from the soil water due to the material itself, and which can be used for collecting soil water which is truly representative of the water contained in the soil being tested.

Although there have been many known substances which may be considered to be inert, to my knowledge none of these have characteristics of moisture transmission which would make them suitable for use in soil water recovery.

There is a type of plastic resins which are basically monomers containing one or more atoms of fluorine or copolymers of such monomers with other monomers, the fluorine-containing monomers being the greater part of the mass. These plastics are called fluoroplastics and have been used as coatings, linings and as components of pumps, fittings, process vessels, etc. Fluoroplastics include polytetrafluoroethylene (PTFE), polyvinyl fluoride (PVF), ethylenechlorofluoroethylene copolymer (ECTFE), polyvinylidene fluoride (PVDF), ethylenetetrafluoroethylene copolymer (ETFE), perfluoroalkosy resin (PFA), and fluorinated ethylene-propylene copolymer (FEP). As now known and used, these resins are neither rigid nor porous. They present a tight barrier to transmission of either liquids or gases. They would clearly be unsuitable for any filtering function.

I have discovered that it is possible to use these fluoroplastic resins as raw materials in a process for preparing synthetic resins which are rigid and porous, which can be molded and machined as filter units in a lysimeter and that a lysimeter which employs such special filter units is much more effective in the collection of soil water which is truly representative in content and character of the moisture contained in the soil at the location selected for test.

BRIEF DESCRIPTION OF THE DRAWINGS

In the drawings, which illustrate embodiments of the invention.

Preparation of the Special Resin

Figure 2:
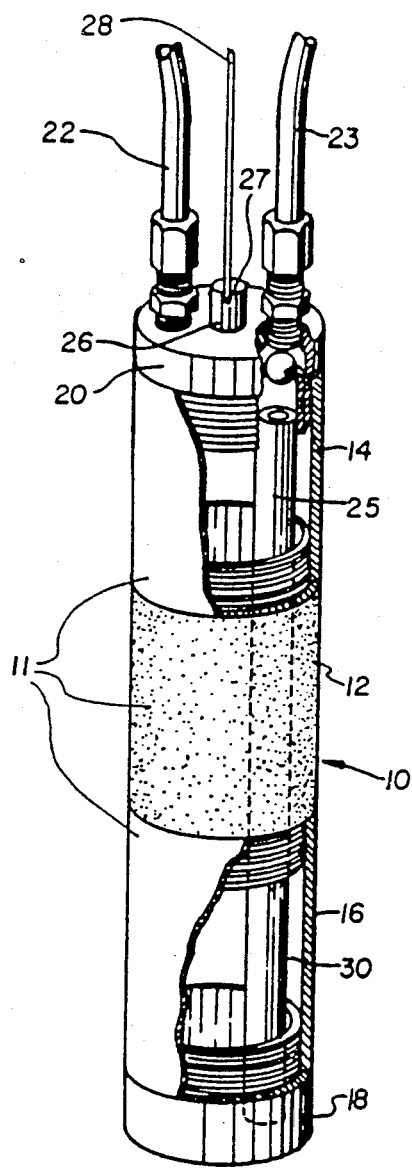
FIG. 2 is a first embodiment of a lysimeter with the filter section of FIG. 1.

As a first step the fluoroplastic raw material such as PTFE is blended with a sacrificial agent. The sacrificial agent is a raw material used in the process but which is totally removed during the course of the process. I prefer to use stearic acid, but other fatty acids or chemicals having vaporization points of the order of 350° to 450° F. under the conditions of the process, may be used.

The fluoroplastic should be powdered form, in particles which will pass a screen of 6 to 100 mesh, preferably 10 to 20 mesh, and the sacrificial agent should also be in powdered form, in particles which will pass a screen of 15 to 325 mesh, preferably a screen of 100 to 200 mesh.

The fluoroplastic resin and the sacrificial agent in a proportion of about 5% to 99% fluoroplastic and about 95% to 1% sacrificial agent, preferably about 80% to 90% resin and 10% to 20% sacrificial agent. Using these preferred proportions it may be expected to produce pores with diameters of the order of about 70 microns. In general lower percentages of sacrificial agent produce a product having a lower degree of porosity and higher percentages of sacrificial agent produce products having a higher degree of porosity. Using the above as a guide, pore sizes of from about 0.004 to about 300 microns may be obtained and used in my process.

The fluoroplastic and the sacrificial agent may be placed together in a rotary screen which, preferably is made of polyvinylchloride, and the mixture thoroughly blended. It is important to avoid lumps in either the fluoroplastic or the sacrificial agent as this would produce faulty areas without pores or passages. The blend thus produced is ready for molding.

Molding of the Blend of Resin and Sacrificial Agent

If it is desired to make the filter in tubular form a suitable size cylindrical mold having a central core, suitably made of polyvinylchloride, may be selected. The mixture is fed into the mold and pressure applied on the mixture. The pressure initially applied should preferably not exceed 3000 p.s.i. but the pressure may be increased to the order of about 5000 p.s.i. and may be held for a time (suitably about 30 second to 1 minute) before being released. The pressed and formed material may be removed from the mold. Some care should be taken in doing this because at this stage the material is somewhat fragile.

Removal of the Sacrificial Agent

After removal of the product from the mold it may be placed in an oven having a relatively low temperature (about 350° F. to 400° F.) and held for a time sufficient to completely volatize the sacrificial agent. For a tubular piece having an O.D. of about 2 inches and about 6" long a time of 2 to 6 hours should be satisfactory. In general, larger pieces take longer times to effect complete vaporization while smaller pieces require less time. When the sacrificial agent is completely volatilized the piece will be seen to have a blackened appearance.

The Sintering Treatment

After the sacrificial agent is completely volatilized from the resin material it may be placed in a relatively high temperature oven having a temperature of about 600° F. to 750° F., preferably about 690° F. for a time (a minimum of about 48 hours) or until the material appears luminescent and semi-transparent, its former blackened appearance having completely disappeared. After this high temperature treatment is complete the material may be allowed to cool (preferably in the oven until it comes to about 400° F.) I find that even if the material is left in the high temperature oven for a longer time than above indicated the material does not change in character and remains usable in a lysimeter in the same way. When the material comes down to substantially ambient temperature it may be machined to prepare it for assembly within a lysimeter. For example, threads (preferably square threads) may be formed on its ends for making attachments to other parts of the lysimeter.

Figure 1:
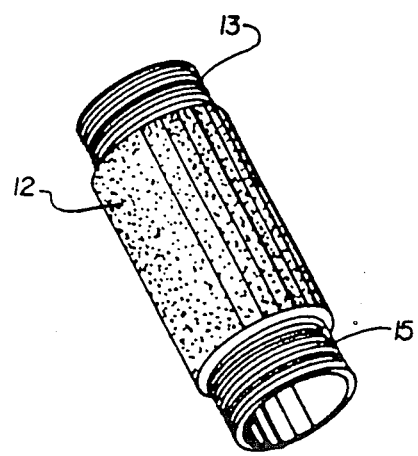
FIG. 1 is the filter section of one embodiment of a lysimeter.

As illustrated in FIG. 2 the lysimeter 10 has a tubular, cylindrical wall 11 in three sections. The central section is the filter 12 which is separately illustrated in FIG. 1. The filter section 12 has square male threads 13 at its top end and threads 13 engaged matching female threads on the lower end of section 14 of the wall 11. At the lower end of the filter 12 are square male threads 15 which engage interior female threads on the inside of the lower wall section 16.

The upper end of wall 11 is female threaded engagement with the top plug 20 and the lower end of wall 11 is female threaded engagement with the bottom plug 18. The chamber 30 of the lysimeter is bounded on its sides with the cylindrical wall 11, on its top by the top plug 20 and on its bottom with the bottom plug 18.

There are two tapped holes in the top plug 20; one end of a tube 22 is connected to one of these holes and extends upwardly of the lysimeter to a source of vacuum or air pressure, and another tube 23 is connected to the other of these holes and extends upwardly to a container at the ground surface where the soil water may be recovered. A tube 25 extends downwardly in the chamber 30 to a point near the bottom plug 18, so that soil water may be passed upwardly through stationary tube 25 and flexible tube 23 to the receptacle 24. A plug having an eyelet 27 at its top is turned into a tapered depression at the top center of the plug 20, and a lowering line 28 may be attached to the eyelet 27 for lowering the lysimeter into a hole bored into the earth at the point where a test is to be made.

The rigid parts of the lysimeter, except for the filter piece 12, may suitably be made of polyvinylchloride or other rigid inert material which can be machined.

Installation of Lysimeter at Site of Test

Figure 4:
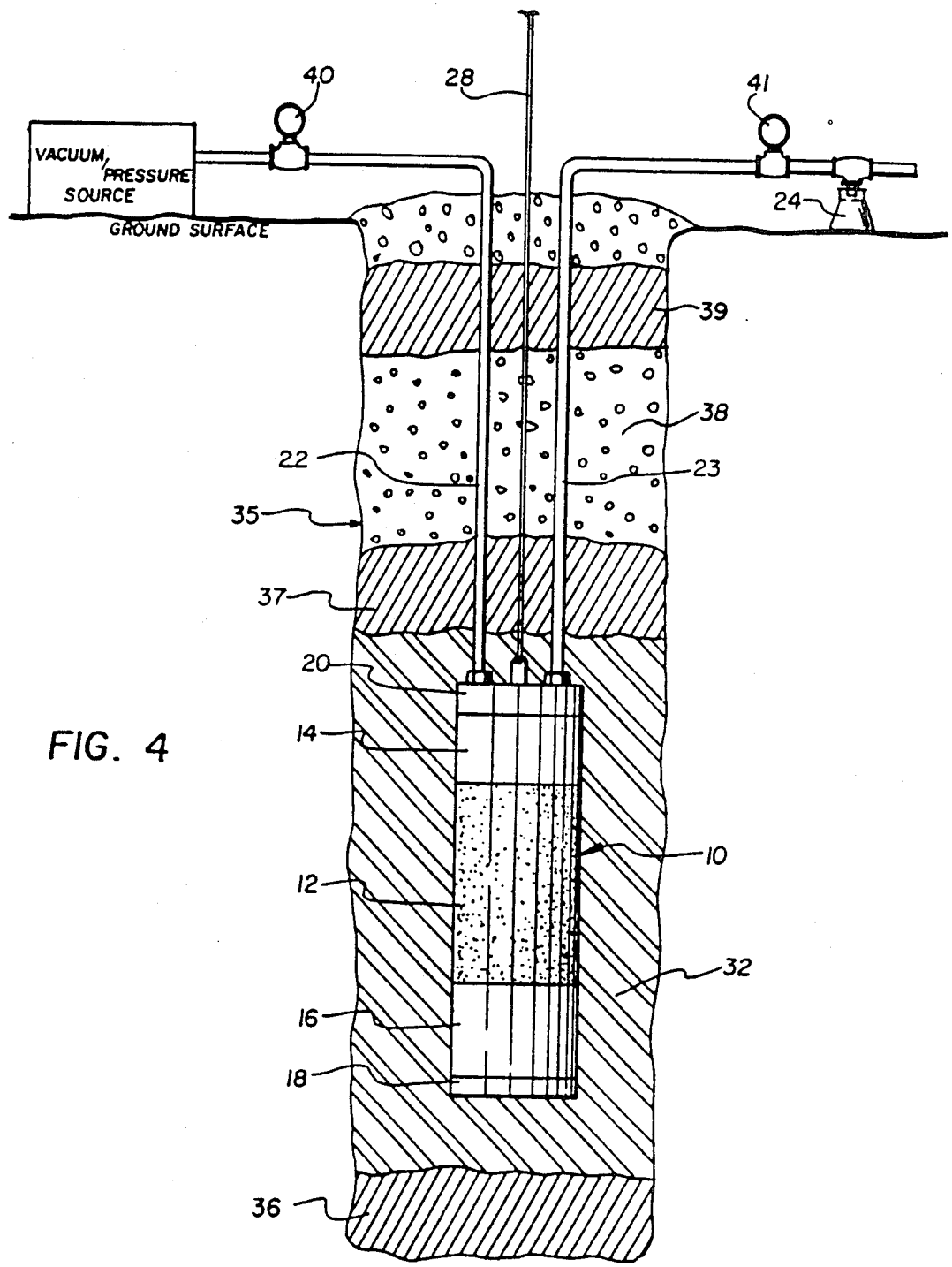
FIG. 4 illustrates the lysimeter of FIG. 2 disposed within a hole bored into the earth.

Reference is now made to FIG. 4 of the drawings. A hole 35 is first bored into the earth at the location of the test cite, the hole being wide enough to receive the lysimeter with space left for filling about the lysimeter. A bentonite layer 36 is placed at the bottom of the hole to form a seal beneath the lysimeter. Using the lowering line 28 the lysimeter is lowered into the hole and a slurry of crystalline silica 32 is put into the hole about the lysimeter, and another bentonite layer 37 is put over the silica to form another seal. Earth backfill 38 is put in over the second seal and a third bentonite seal 39 is placed over the earth backfill.

The valves 40 and 41 control passage through tubes 22 and 23 respectively.

Recovery of Soil Water Using the Improved Lysimeter

With tube 23 closed against passage into the lysimeter a vacuum of about 18 to 20 inches of mercury is applied to tube 22. With this condition soil water is drawn through the silica to and through the wall of filter 12 into the chamber 30 of the lysimeter. After about a day the vacuum may drop and a sample may be drawn from the chamber. This may be accomplished by opening the line to tube 22 and applying a vacuum to tube 23. The process may then be repeated until soil water is obtained for purposes of analysis. The first water drawn from the lysimeter, (equivalent to the water originally contained in the slurry) maybe discarded, and the soil water subsequently recovered will be found truly representative of the character of the soil water in the area under investigation.

Figure 3:
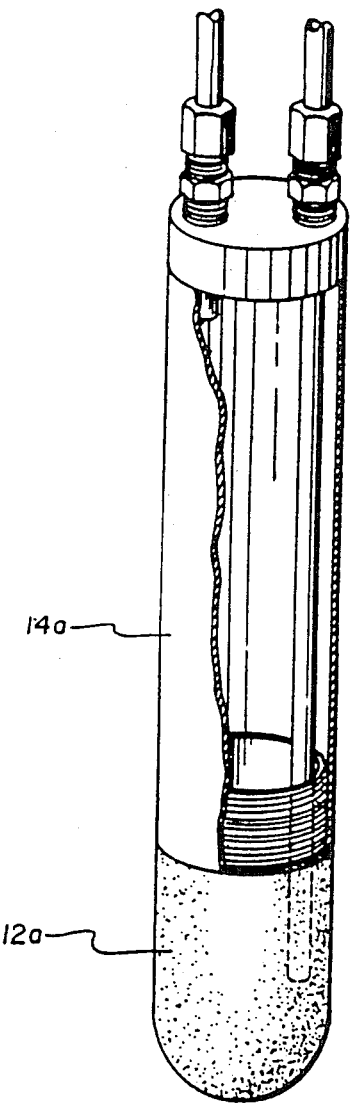
FIG. 3 is a second embodiment of a lysimeter.

Similar tests may be run using the lysimeter of FIG. 3 in a similar manner to obtain soil water truly representative of the area under investigation. The cup type filter section 12a of the type illustrated in FIG. 3 may be made in the same way as described in connection with the filter section 1 except for using a mold which yields the cup shaped filter. In the assembly of the cup shaped filter in the lysimeter the filter 12a which has male threads at its top may be turned into the threads on the inside of the upper section 14a.

To further demonstrate the manufacture of the improved fluoroplastic resin material and its use and operation in the improved lysimeters, I include the following specific examples:

EXAMPLE 1

Blending of Raw Materials

I obtained from the Dupont Chemical Company a quantity of powdered polytetrafluoroethylene resin which is a fluoroplastic resin designated as product "type 7A" marketed under the trademark Teflon and obtained also a quantity of stearic acid also in powdered form for use as a sacrificial agent.

These raw materials were placed in a room maintained under positive pressure and filtered air, to minimize dust. The resin and stearic acid were weighed out to make a mixture of 85% resin and 15% stearic acid using plastic containers and utensils. The resin and stearic acid were placed in a single container and stirred gently. After stirring, the mixture was placed inside a rotary polyvinyl screen (with slots 0.050 inches wide cut inrows about the tube) and a pan was placed under the screen to catch the material which would pass the screen. The screened and blended collected material was passed to the molding operation.

EXAMPLE 2

Molding of the Blend

A tubular mold made of polyvinyl chloride having a 1½ inch diameter was selected and the blended powder was filled into the mold. Pressure was applied and increased gradually to 3000 p.s.i., then increased to 5000 p.s.i. for about a minute to get out any trapped air. The pressure was then released and the filter piece removed from the press and passed to the volatilization step.

EXAMPLE 3

Volatilization of the Sacrificial Agent

The shaped and pressed filter piece would hold together but at this stage it was somewhat fragile and not to be dropped. The filter piece was placed on end in an oven at a relatively low temperature (in this case at about 400° F.). If more than one piece was being treated, space would be left between the pieces. The oven was set at 400° F. and after about 4 hours the material had a uniform blackened appearance. If at the end of this period the material did not have the uniform dull blackened appearance we would have left it for an additional period to time. Or if the material showed white, or colored spots we would have extended the time of heat treatment at about 400° F. Next we allowed the filter piece to cool. We kept the filter piece in the low temperature oven with the door closed until the temperature was substantially reduced because we found that too rapid cooling could cause checking of the outer surfaces. At the end of the low temperature treatment the blackened filter material still was somewhat fragile.

EXAMPLE 4

The Sintering Treatment

After the heat treatment at about 400° F. the cooled filter was set on end in the high temperature oven set at 690° F. The oven we used had an air flow exchange of 240 cu. ft. per minute. After 48 hours the door was opened for inspection, at that time the material appeared to be milky white, somewhat luminescent and semi-transparent. If this appearance had not been uniform and all the blackness had not disappeared, we would have continued the 690° F. treatment. The piece should be uniformly luminescent and semitransparent. We left the filter piece cool in the oven door with the door shut until the oven came almost to ambient temperature. The sintered piece was smooth and hard.

EXAMPLE 5

Machining

After the high temperature sintering step the filter piece was machined by threading the ends, providing square threads on each end. The sintered filter was porous and contained pores averaging about 70 microns in diameter. It was hard and rigid.

EXAMPLE 6

Assembly in a Lysimeter

The machined sintered filter was then assembled with other parts of a lysimeter, the treads on each end being turned into engagement with corresponding internal threads in tubular parts of the lysimeter, such other parts being made of polyvinyl chloride.

EXAMPLE 7

Test of Capability of the Improved Filter to Pass Water Therethrough and Comparison with the Known Ceramic Lysimeter The purpose of this test was to compare the operation of the improved lysimeter of this invention using the porous rigid fluoroplastic filter with the operation of lysimeters previously available using a porous ceramic filter.

Two lysimeters which were identical except that one had a porous ceramic filter cup and the other had a porous, rigid fluoroplastic filter cup as described in the present specification. Each lysimeter was installed in identical 32 gallon plastic containers. Three holes had been drilled in the sides for later access to the media for laboratory determination of moisture content by ASTM 02216-60 Standards. Both containers were filled with silica sand as the media having a predetermined moisture content of 1.1%. In each installation 30 lbs. of 99.88% pure silica flour was mixed with (150 ml. per lb.) distilled water. The lysimeters were evacuated daily and the test ran for 50 consecutive days. The porous fluoroplastic lysimeter totaled 2020 mls. of recovered water while the ceramic lysimeter yielded 1648 mls. of recovered water the recovery by the fluoroplastic lysimeter being 18% greater. There was some fluctuation in pH but the fluoroplastic lysimeter samples held more closely to the original 6.5 pH than did the ceramic lysimeter. Performance was judged to be markedly better in the case of the fluoroplastic lysimeter.

While I have described in detail only certain embodiments of my invention, it will be apparent that many other embodiments may be constructed and demonstrated, and many changes may be made, all within the spirit of the invention and the scope of the appended claims.

What is claimed is:

1. A lysimeter containing a chamber having a wall containing a filter section which is formed of fluoroplastic resin, said resin being rigid and porous and capable of passing moisture therethrough.

2. A lysimeter as set forth in claim 1 in which said filter section is made of polytetrafluoroethylene.

3. A lysimeter as set forth in claim 1 in which said chamber is bounded by a cylindrical wall and in which said wall contains a central filter section which is formed of rigid porous fluoroplastic resin.

4. A lysimete as set forth in claim 3 in which said fluoroplastic resin is polytetrafluoroethylene.

5. A process for recovering soil water comprising making a hole in the earth at a location from which soil water is to be recovered, lowering into said hole a lysimeter having a chamber and a wall bordering said chamber, one section of said wall constituting a filter, said filter section being of porous rigid fluoroplastic resin, and withdrawing through a tube connected with said chamber soil water which has passed through said filter section into said chamber.

6. A process as set forth in claim 5 in which said filter section is rigid porous polytetrafluoroethylene.

7. A process as set forth in claim 5 including the step of drawing a vacuum on said chamber through a tube connected with said chamber to urge soil water through said filter section into said chamber.

8. A process as set forth in claim 5 which includes lowering into said hole a lysimeter containing said chamber, placing a slurry of crystalline silica in said hole about said lysimeter prior to withdrawal of soil water from said chamber.

* * * * *